United States Patent [19]

Rudolph et al.

[11] Patent Number: 4,912,263

[45] Date of Patent: Mar. 27, 1990

[54] IONIC EXCHANGERS MODIFIED WITH THIAZOLINES

[75] Inventors: Udo Rudolph; Claus Wulff; Jürgen Hinz; Norbert Bachem, all of Krefeld, Fed. Rep. of Germany

[73] Assignee: Bayer Aktiengesellschaft, Leverkusen, Fed. Rep. of Germany

[21] Appl. No.: 230,316

[22] Filed: Aug. 9, 1988

[30] Foreign Application Priority Data

Aug. 19, 1987 [DE] Fed. Rep. of Germany ....... 3727641

[51] Int. Cl.$^4$ ............................................. C07C 39/12
[52] U.S. Cl. .................................. 568/722; 568/723; 568/727; 521/32
[58] Field of Search ................. 521/32; 568/723, 727, 568/722

[56] References Cited

U.S. PATENT DOCUMENTS 3,634,341 1/1972 Gammill et al. ...................... 521/32
4,239,919 12/1980 Hairston ............................... 568/727
4,369,293 1/1983 Heydenreich .
4,396,728 8/1983 Faler .
4,634,726 1/1987 Martin .................................... 524/34

FOREIGN PATENT DOCUMENTS 0023325 2/1981 European Pat. Off. .
2422532 11/1975 Fed. Rep. of Germany .
1183564 3/1970 United Kingdom .

Primary Examiner—Joseph L. Schofer
Assistant Examiner—Peter F. Kulkosky
Attorney, Agent, or Firm—Connolly and Hutz

[57] ABSTRACT

This invention relates to an ionic exchanger modified with thiazolines, to its preparation and to its use for the preparation of condensation products, particularly bisphenols.

4 Claims, No Drawings

IONIC EXCHANGERS MODIFIED WITH THIAZOLINES

This invention relates to an ionic exchanger modified with thiazolines and to its use for the preparation of condensation products, particularly bisphenols.

The condensation of phenols and carbonyl compounds to form bisphenols is known. Various catalysts have already been used for this reaction, for example hydrochloric acid (U.S. Pat. Nos. 2,182,308 and 2,191,831), boron trifluoride (Chemical Abstracts 58, 3338 c), perchloric acid (Chemical Abstracts 60, 1626 h), benzene sulphonic acid (Chemical Abstracts 59, 511 h) and numerous cation exchange resins (e.g. GB-PS Nos. 842 209, 849 565 and 883 391). The addition of compounds containing sulphur to the catalyst is also known, e.g. the use of thioglycolic acid and 3-mercapto-proprionic acid has been disclosed in U.S. Pat. Nos. 2,468,982 and 2,623,908, the addition of thiophenols in U.S. Pat. No. 2,359,242, the addition of alkyl mercaptans in U.S. Pat. No. 2,775,620 and the addition of hydrogen sulphide in Chemical Abstracts 58, 1403 e.

The known catalysts containing sulphur may cause considerable damage by corrosion in industrial use. The bisphenols prepared with the aid of these catalysts are impure. The crude products contain not only bisphenol but also unreacted phenol, carbonyl compound, water of reaction and undesirable by-products. The crude products obtained from the synthesis of bisphenol A, for example, contain isomers of bisphenol A, in particular 2,2-(2,4'-dihydroxydiphenyl)-propane and 2,2-(2,2'-dihydroxydiphenyl)-propane, complex products such as the so called "codimers", 2,2,4-trimethyl-4-p-hydroxyphenylchroman, and condensation products such as trisphenol or even higher condensation products in the form of tarry or high boiling substances. The presence of these by-products is undesirable as they tend to remain in the end product and cause discolourations. In some cases, these by-products also cause considerable difficulties in processing the products.

The by-products also prevent some of the usual reactions of bisphenol, in particular its further conversion to polycarbonates.

U.S. Pat. No. 3,394,089 describes a process for the preparation of bisphenol A from acetone and phenol using a catalyst containing sulphonic acid groups, 5 to 25 mol % of which sulphonic acid groups are blocked with mercapto amines to form ammonium salts in order to avoid the aforesaid disadvantages. This modified ion exchanger resin, however, which is obtained by neutralization in aqueous solution, for example with β-mercaptoethylamine, gives rise to problems when employed on a large technical scale because it is unstable and the mercapto compound is washed out by the reaction medium in the course of prolonged use.

It has now been found that strongly acid ion exchangers in which the acid groups are neutralized to a high degree or even quantitatively and neutralization is carried out with previously dried ion exchanger in a anhydrous medium are very suitable, for example, for the preparation of highly pure bisphenols.

The present invention therefore relates to an ion exchanger which is modified with thiazolines, characterised in that known acid ion exchange resins which have total capacities of acid functions of from 0.7 to 2.1 mval/ml of ion exchanger when they are in a water moist form with a water content of about 75 to 85% by weight or total capacities of acid functions of from 3.5 to 5 mval of ion exchanger, based on 1 g of dry substance, are dried, then rinsed with the phenol to be used for the preparation of the bisphenol and thereafter neutralized with at least 0.3 mol, preferably from 0.4 to 1 mol of thiazolines of formula (I) per mol of acid function of the ion exchanger at a temperature above the melting point of the phenol.

At least 10 mol %, preferably from 20 to 100 mol % of the acid functions of this modified ion exchanger are neutralized with the thiazoline corresponding to formula (I):

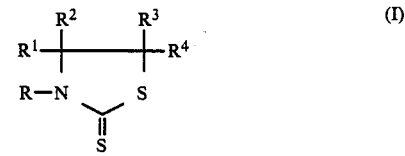

wherein R, $R^1$ $R^2$, $R^3$ and $R^4$ denote, independently of one another, hydrogen, a $C_1$ to $C_6$ alkyl group, a $C_5$ to $C_{10}$ cycloalkyl group or a $C_6$ to $C_{14}$ aryl group.

Examples of suitable acid ion exchangers include the ordinary (commercial) products of reaction of styrenedivinyl benzene copolymers with conventional sulphonating agents such as sulphuric acid, chlorosulphonic acid, etc. The ion exchangers may be in spherical form with particle sizes of from 0.3 to 1.5 mm in diameter. They may be of the gel type or macroporous. Their total capacity for acid functions in the aqueous form with a water content of about 75 to 85% by weight ranges from 0.7 to 2.1 mval/ml of ion exchanger or it ranges from 3.5 to 5 mval, based on 1 g of dry ion exchanger substance.

These ion exchangers are optionally dried by heat, optionally in a vacuum or optionally by washing with hydrophilic organic liquid such as alcohols or phenols or by azeotropic distillation with organic liquid such as phenol, toluene, xylene, methylene chloride, etc. The ion exchanger resin is then rinsed with the phenol required for the preparation of the bisphenol, and the desired quantity of thiazoline of formula (I) is then added in this medium at temperatures above the melting point, with stirring or in a fluidized bed layer.

The thiazoline of formula (I) used for the reaction is preferably 2-mercapto-thiazoline.

The cation exchange resin modified by neutralization may be used for the preparation of numerous bisphenols from phenols and carbonyl compounds.

Suitable phenols are, for example, those corresponding to formula (II):

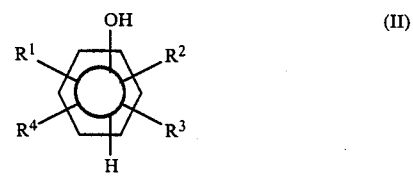

wherein
$R^1$, $R^2$, $R^3$ and $R^4$ denote, independently of one another, hydrogen (H), $C_1$ to $C_4$ alkyl or halogen such as F, Cl or Br.

The following are examples: 2,6-dimethylphenol, o- and m-cresol, o-sec-butylphenol, o-tert.-butylphenol, 1,3,5-xylenol, 2,6-di-tert.-butylphenol, tetramethylphenol, 2-methyl-6-tert.-butylphenol, o-phenylphenol, o- and m-chlorophenol, o-bromophenol, 6-chloro-o-cresol and 2,6-dichlorophenol.

Unsubstituted phenol is preferred.

Suitable carbonyl compounds include those corresponding to formula (III):

$$R^1-\underset{\underset{R^2}{|}}{C}=O \quad \text{(III)}$$

wherein $R^1$ and $R^2$ denote, independently of one another, hydrogen (H), $C_1$ to $C_6$ alkyl, $C_6$ to $C_{10}$ cycloalkyl, $C_6$ to $C_{14}$ aryl, $C_7$ to $C_{20}$ aralkyl or $C_7$ to $C_{20}$ alkylaryl or $R^1$ and $R^2$ together form a saturated ring with 5 to 6 ring atoms.

Examples of suitable carbonyl compounds include aldehydes and ketones such as formaldehyde, methylethylketone, methylpropylketone, diethylketone, cyclohexanone, acetophenone, etc. Acetone is preferred.

Reaction of the carbonyl compounds of formula (III) with phenols of formula (II) in the presence of ion exchangers may be carried out continuously or intermittently. The method of procedure and the apparatus required are known.

For a discontinuous process, the ion exchanger resin according to the invention is used in a quantity corresponding to 80 to 200 g, preferably 100 to 150 g of dry substance per mol of carbonyl compound.

The reaction temperature for the preparation of the bisphenols is in the range of from 40° to 120° C., preferably above the solidification point of the components.

The reaction time or residence time is chosen to provide for complete conversion of the carbonyl compound. It is preferably from 30 to 240 minutes.

The present invention therefore also relates to the use of the ion exchangers modified with thiazolines of formula (I) obtainable according to the invention for the preparation of bisphenols from phenols and carbonyl compounds.

The reaction mixture obtained after the reaction of phenol and carbonyl compound is worked up by the usual methods such as distillation, crystallization, etc.

Thus for example the bisphenol obtained may be cooled in the reaction mixture until crystallization sets in and the phenol may then be removed by distillation or extraction from the mixed crystals of bisphenol and phenol which have been filtered off.

The bisphenol prepared by this process may be used for known fields of application without further purification and is also suitable for very high standard work such as the preparation of optically very pure polycarbonates.

EXAMPLE 1

Preparation of the Modified Ion Exchange Resin

Ion exchanger as supplied in a water moist form with a moisture content of about 80% by weight and a total capacity of 0.75 mval/ml is first washed with distilled water. The resin is then dried at 90° to 100° C. in a water jet pump vacuum for 24 hours to reduce the water content below 1% by weight.

The residual water is distilled off as an azeotropic mixture with toluene and any toluene adhering to the ion exchange resin is then distilled off in a water jet pump vacuum at 95° C.

120 g of the ion exchange resin which has been pretreated as described above are introduced into 1128 g of phenol in a stirrer apparatus and left to swell for 24 hours at 65° C. with exclusion of moisture. The quantity of 2-mercaptothiazoline required to give the particular content in mol % indicated in Examples 2 to 10 is then added with stirring.

EXAMPLES 2 TO 10

Preparation of Bisphenol A (BPA)

The ion exchange resin was modified with 2-mercaptothiazolidine by the process described in Example 1 so that from 15 to 100% of the sulphonic acid group were neutralized in nine adjustments. 58 g of acetone at 65° C. were added in each case to the solution prepared in Example 1 and after complete conversion of the acetone the gas chromatographic purity of the bisphenol or the quantity of by-products was determined. The following table summarizes the results in the form of average values obtained from 5 experiments per example.

| Example | Content | GC Surface Percent BPA | By-Product |
|---|---|---|---|
| 2 | 15 | 93.1 | 6.9 (comparison) |
| 3 | 20 | 93.5 | 6.5 (comparison) |
| 4 | 25 | 93.7 | 6.3 (comparison) |
| 5 | 30 | 94.1 | 5.9 |
| 6 | 40 | 94.6 | 5.4 |
| 7 | 50 | 95.1 | 4.9 |
| 8 | 60 | 95.7 | 4.3 |
| 9 | 80 | 96.7 | 3.3 |
| 10 | 100 | 97.2 | 2.8 |

We claim:

1. Ion exchanger modified with thiazoline, characterized in that acid ion exchange resins which have total capacities of acid functions of from 0.7 to 2.1 mval/ml of ion exchanger in their water moist form with a water content of about 75 to 85% by weight or total capacities of acid functions of from 3.5 to 5 mval based on 1 g of dry substance of ion exchanger are dried and thereafter rinsed with a phenol to be used for the preparation of a bisphenol and then neutralized with at least 0.3 mol of thiazolines of formula (I)

$$\underset{\underset{\underset{S}{\|}}{S}}{R-N}\diagup\diagdown\overset{\overset{R^2\quad R^3}{|\quad\;|}}{\underset{}{\overset{R^1}{\diagdown}\text{—}\overset{R^4}{\diagup}}} \quad \text{(I)}$$

per mol of the ion exchanger at a temperature above the melting point of the phenol, wherein each of R, $R^1$, $R^2$, $R^3$ and $R^4$, independent of one another, is hydrogen, alkyl having 1 to 6 carbon atoms, cycloalkyl having 5 to 10 carbon atoms or aryl having 6 to 14 carbon atoms.

2. Ion exchanger according to claim 1, characterised in that neutralization is carried out with from 0.4 to 1 mol of thiazolines of formula (I).

3. In the process for production of phenolic condensation products of phenols and carbonyl compounds, the improvement comprises reacting the phenol with the carbonyl compound in the presence of an ion exchanger as claimed in claim 1.

4. The process according to claim 3 wherein the phenolic condensation product is bisphenol -A.

* * * * *